United States Patent
Hammoud et al.

(10) Patent No.: US 7,578,593 B2
(45) Date of Patent: Aug. 25, 2009

(54) EYE MONITORING METHOD WITH GLARE SPOT SHIFTING

(75) Inventors: Riad I. Hammoud, Kokomo, IN (US); Andrew P. Harbach, Kokomo, IN (US)

(73) Assignee: Delphi Technologies, Inc., Troy, MI (US)

( * ) Notice: Subject to any disclaimer, the term of this patent is extended or adjusted under 35 U.S.C. 154(b) by 334 days.

(21) Appl. No.: 11/444,841

(22) Filed: Jun. 1, 2006

(65) Prior Publication Data

US 2007/0279588 A1    Dec. 6, 2007

(51) Int. Cl.
*A61B 3/00* (2006.01)
*A61B 3/14* (2006.01)
*A61B 3/10* (2006.01)

(52) U.S. Cl. .................. 351/246; 351/206; 351/209; 351/221

(58) Field of Classification Search ............. 351/206, 351/205, 209, 210, 221, 246
See application file for complete search history.

(56) References Cited

U.S. PATENT DOCUMENTS

| 5,598,145 A | 1/1997 | Shimotani |
| 2002/0181774 A1 | 12/2002 | Ishikura |
| 2005/0270486 A1 | 12/2005 | Teiwes et al. |

OTHER PUBLICATIONS

EP Search Report dated Sep. 20, 2007.

*Primary Examiner*—William C Choi
*Assistant Examiner*—Jack Dinh
(74) *Attorney, Agent, or Firm*—Jimmy L. Funke

(57) ABSTRACT

The face of a human subject is alternately illuminated by first and second sources of active illumination disposed above and below a video camera that captures images of the subject's face. Glare due to reflection of the active illumination from eyeglasses worn by the subject shifts up or down from one image to the next due to the different locations of the first and second sources. Eye detection and tracking routines ignore images in which the eye is occluded by eyeglass glare so that the glare does not interfere with the performance of the routines.

3 Claims, 5 Drawing Sheets

EYE MONITORING METHOD WITH GLARE SPOT SHIFTING

TECHNICAL FIELD

The present invention relates to monitoring a human's eyes in a video image, and more particularly to a method and apparatus for producing images of the eye that are not occluded by eyeglass glare.

BACKGROUND OF THE INVENTION

Vision systems frequently entail detecting and tracking a subject's eyes in an image generated by a video camera. In the motor vehicle environment, for example, a camera can be used to generate an image of the driver's face, and portions of the image corresponding to the driver's eyes can be analyzed to assess drive gaze or drowsiness. See, for example, the U.S. Pat. Nos. 5,795,306; 5,878,156; 5,926,251; 6,097,295; 6,130,617; 6,243,015; 6,304,187; and 6,571,002, incorporated herein by reference.

Due to variations in ambient lighting, the vision system typically includes a bank of infrared lamps that are lit during the image capture interval of the camera to actively illuminate the driver's face. While such active lighting ensures that the driver's face will be sufficiently illuminated to enable the camera to produce a high quality image, it can also introduce glare that occludes the eye when the driver is wearing eyeglasses. Such eyeglass glare is troublesome because it can interfere with the operation of the vision system's eye detection and tracking algorithms. It may be possible to remove eyeglass glare from an image, but this typically adds a significant amount of image processing, which may be impractical in a system that already is burdened with complex image processing routines. Accordingly, what is needed is a way of producing high quality eye images that are not occluded by eyeglass glare.

SUMMARY OF THE INVENTION

The present invention is directed to a novel method and apparatus for producing a stream of video images of an actively illuminated human eye, where glare due to eyeglass reflection is shifted in a way that allows accurate and efficient eye detection and tracking. First and second sources of active illumination are physically staggered, and preferably disposed above and below a video imaging device. The first and second sources alternately illuminate the subject in successive image capture intervals of the imaging device to produce a stream of video images in which eyeglass glare, if present, shifts from one image to the next. The eye detection and tracking routines are designed to ignore images in which the eye is occluded by eyeglass glare so that the glare does not interfere with the performance of such routines.

DESCRIPTION OF THE PREFERRED EMBODIMENT

The method of the present invention is disclosed in the context of a system that monitors a driver of a motor vehicle. However, it will be recognized that the method of this invention is equally applicable to other vision systems that monitor a human eye, whether vehicular or non-vehicular.

Figure 1:
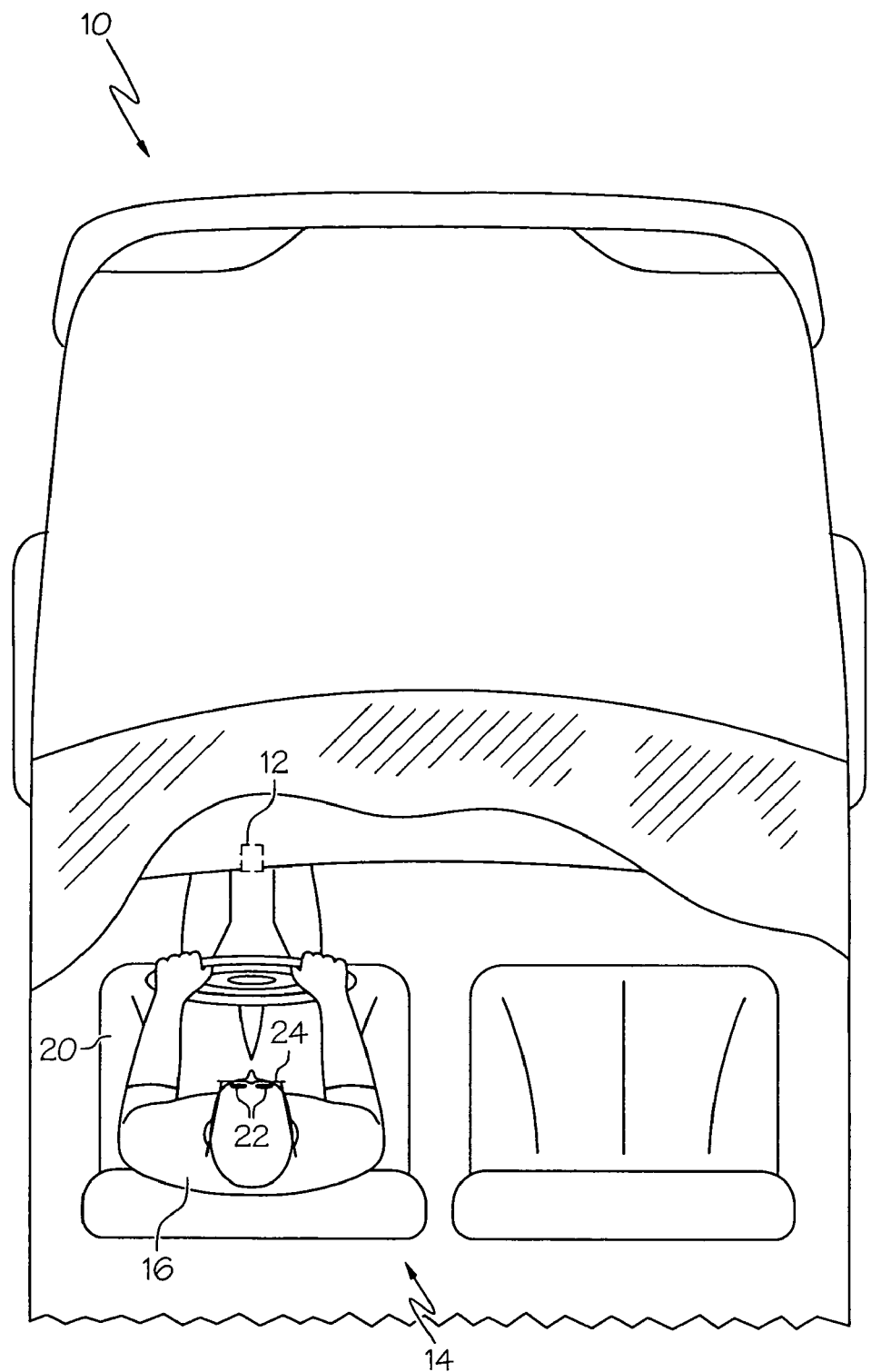
FIG. 1 depicts a diagram of a vehicle equipped with an eye monitoring apparatus according to the present invention.

Referring to the drawings, and particularly to FIG. 1, the reference numeral 10 generally designates a motor vehicle equipped with an eye monitoring apparatus 12 according to the present invention. In the illustration of FIG. 1, the apparatus 12 is mounted in the passenger compartment 14 forward of the driver 16 in a location that affords an unobstructed view of the driver's face 18 when the driver 16 is reposed on the seat 20, taking into account differences in driver height and orientation. In general, the eye monitoring apparatus 12 actively illuminates the driver's face 18 and produces a stream of video images that include the driver's eyes 22. The images are processed to locate the driver's eyes 22 and to track the eye locations from one image to the next. The state of the eyes 22 can be characterized for various purposes such as detecting driver drowsiness and/or distraction, or even driver gaze.

In the illustration of FIG. 1, the driver 16 is wearing eyeglasses 24, which in general may include sunglasses, goggles, or even a face shield. The eyeglasses 24 introduce the potential for glare in the images produced by eye monitoring apparatus 12 due to reflected active illumination that occludes one or both of the driver's eyes 22. While conventional eye monitoring systems are frustrated by eye-occluding glare, the eye monitoring apparatus 12 of the present invention is utilizes a glare shifting technique to enable effective eye detection and tracking in spite of the eyeglass glare.

Figure 2:
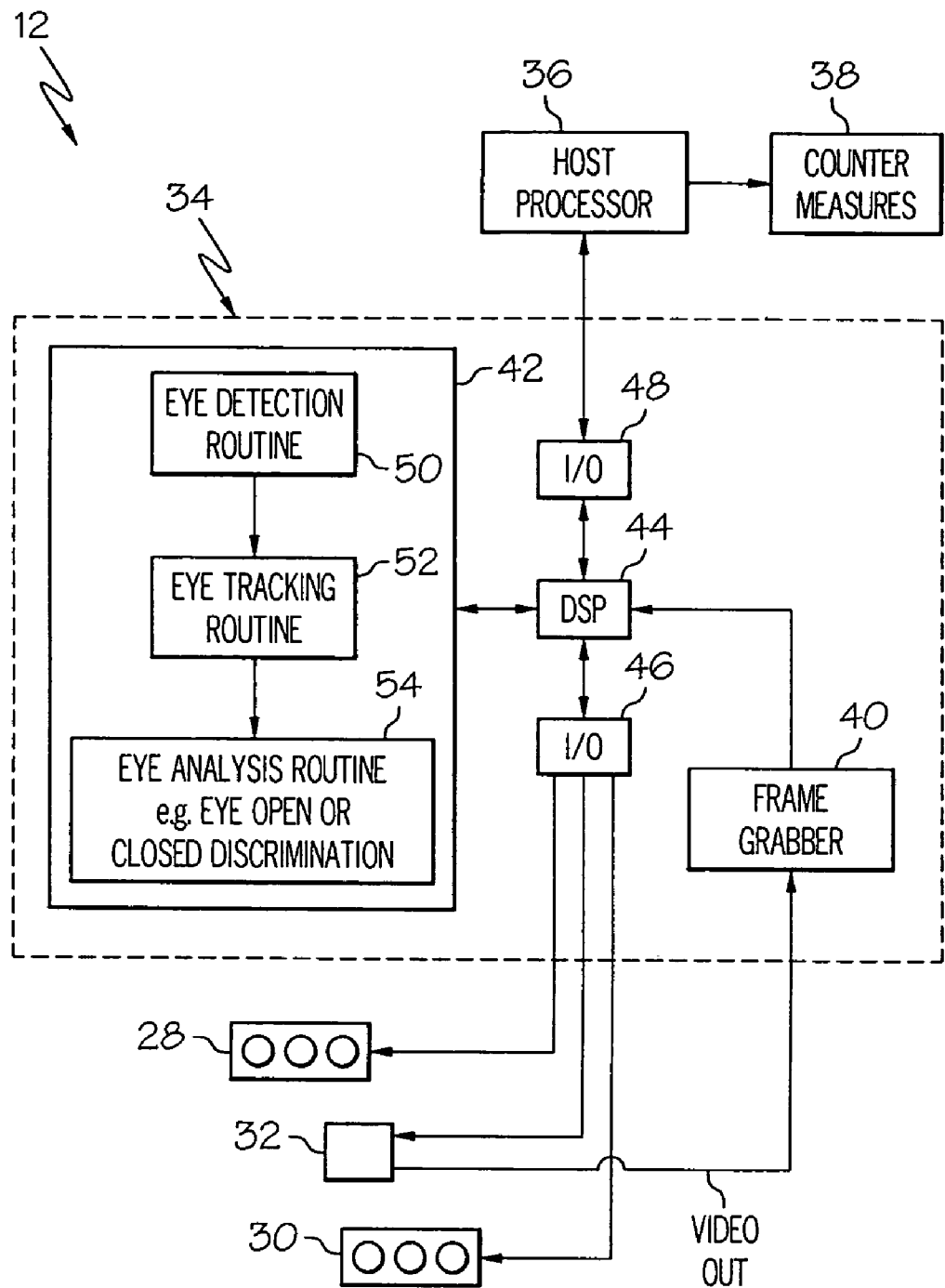
FIG. 2 is a block diagram of the eye monitoring apparatus of FIG. 1, including upper and lower illumination sources, a video imaging device and a microprocessor-based digital signal processor (DSP) for carrying out eye detection and tracking routines.

Referring to the block diagram of FIG. 2, the eye monitoring apparatus 12 includes upper and lower infrared (IR) active illumination devices 28 and 30, a solid-state imaging device 32 focused on the driver's face 18, and a vision processor 34. In the illustrated embodiment, the apparatus 12 provides eye state information to a remote host processor 36 via line 37, and the host processor 36 selectively activates one or more counter-measure devices or systems 38 such as an alarm or a braking system if it is determined that the driver's lack of alertness or attention may possibly compromise vehicle safety. The active illumination devices 28 and 30 are individually activated by the vision processor 34 via I/O interface 46, and each comprises an array of infrared light emitting diodes as indicated. The vision processor 34 comprises conventional components, including a frame grabber 40 for acquiring video images from imaging device 32, a non-volatile memory 42 for storing various signal processing routines, and a digital signal processor (DSP) 44 for selectively executing the routines stored in memory 42 processing the video images acquired by frame grabber 40. The DSP 44 outputs various control signals to illumination device 30 and imaging device 32 via interface 46, and communicates with host processor 37 via interface 48.

The upper and lower active illumination device 28 and 30 are oppositely staggered about imaging device 32 in the vertical direction as indicated in FIG. 2, and are alternately activated during successive image capture intervals of imaging device 32. Due to the proximity of the imaging device 32 to the active illumination devices 28 and 30, the active illumination can reflect off the driver's eyeglasses 24 in a way that creates a glare spot (i.e., a grouping or blob of saturated pixels) in the images produced by imaging device 32. However, the location of the glare spot in the image shifts depending on which active illumination device is lit. For example, if the image produced when the upper active illumination device 28 is lit results in a glare spot that occludes one or both of the driver's eyes 22, the glare spot will be shifted to a non-occluding location in the next image which is produced with driver illumination provided by the lower active illumination device 30.

In general, the active illumination devices 28 and 30 must be physically separated or staggered to achieve the desired glare spot shifting, and the separation distance is preferably on the order of 100 mm or greater. While the active illumination devices 28 and 30 may be staggered horizontally, vertically, or both horizontally and vertically, vertical staggering is preferred for at least two reasons. First, normal eyeglass curvature is such that the amount of glare shift for a given separation between the active illumination devices 28 and 30 occurs when they are vertically staggered. And second, vertical staggering of the active illumination devices 28 and 30 results in vertical shifting of the glare spot, which is the most effective way to shift the spot away from a feature such as an eye that is dominated by horizontal geometry. Also, it is preferred to oppositely stagger the active illumination devices 28 and 30 about the imaging device 32 as shown in FIG. 2 in order to maximize the separation distance for a given package size of eye monitoring apparatus 12.

The signal processing routines residing in the vision processor memory 42 include an eye detection routine 50, an eye tracking routine 52, and an eye analysis routine 54. In general, the routine 50 identifies the regions of a video image that correspond to the driver's eyes 22, the routine 52 tracks the eye location from one video image to the next, and the routine 54 characterizes the state of the driver's eyes (open vs. closed, for example). The eye detection routine and eye tracking routine 50 and 52, as well as the analysis routine 54 and the routines executed by host processor 36 for using the eye state information, may comprise any of a number of known processing techniques. As explained below, however, the eye detection and tracking routines 50 and 52 are capable of detecting and tracking the driver's eyes 22 based on every other image, and ignoring the intermediate images in cases where eye-occluding glare occurs.

Figure 3:
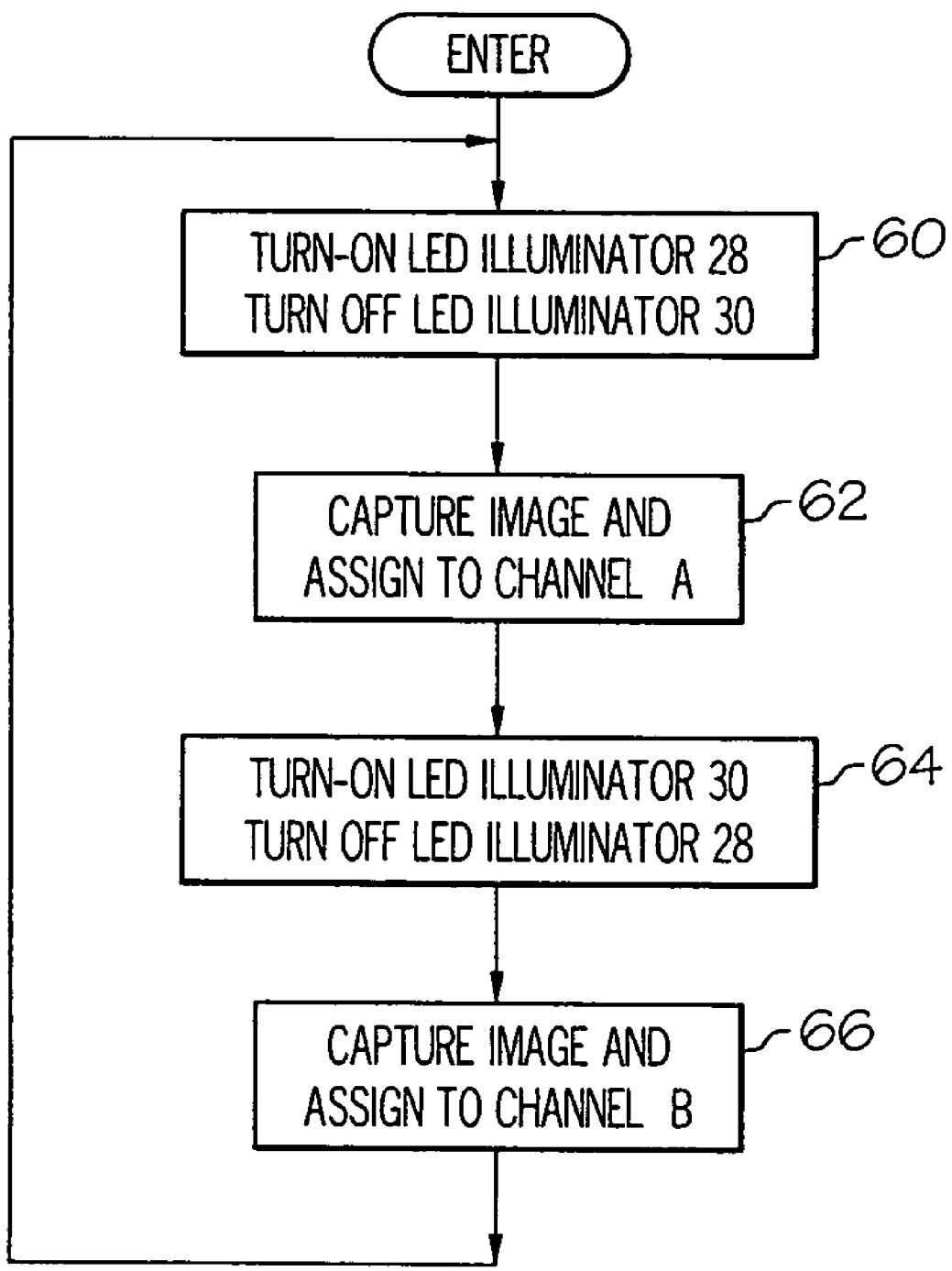
FIG. 3 is a flow diagram representative of an executive routine carried out by the DSP of FIG. 2 for controlling the upper and lower illumination sources and the imaging device.

The flow diagram of FIG. 3 illustrates a coordinated control of active illumination devices 28 and 30 and imaging device 32 by DSP 44. The blocks 60-66 are repeatedly executed as shown to assign the images captured by imaging device 32 to one of two channels, designated as Channel_A and Channel_B. The blocks 60-62 illuminate the driver 16 with just the upper illumination device 28, and then capture the resulting image and assign it to Channel_A. The blocks 64-66 then illuminate the driver 16 with just the lower illumination device 30, capture the resulting image and assign it to Channel_B. Thus, Channel_A contains a stream of images where the driver 16 is actively illuminated by upper illumination device 28, and Channnel_B contains a stream of images where the driver 16 is actively illuminated by lower illumination device 30.

Figure 4:
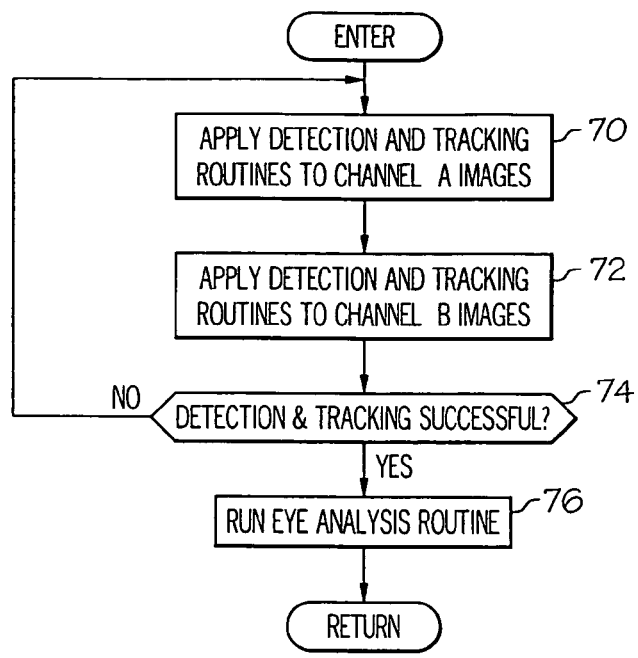
FIG. 4 is a flow diagram representative of an executive routine carried out by the DSP of FIG. 2 for processing the acquired images according to first embodiment of the present invention.
Figure 5:
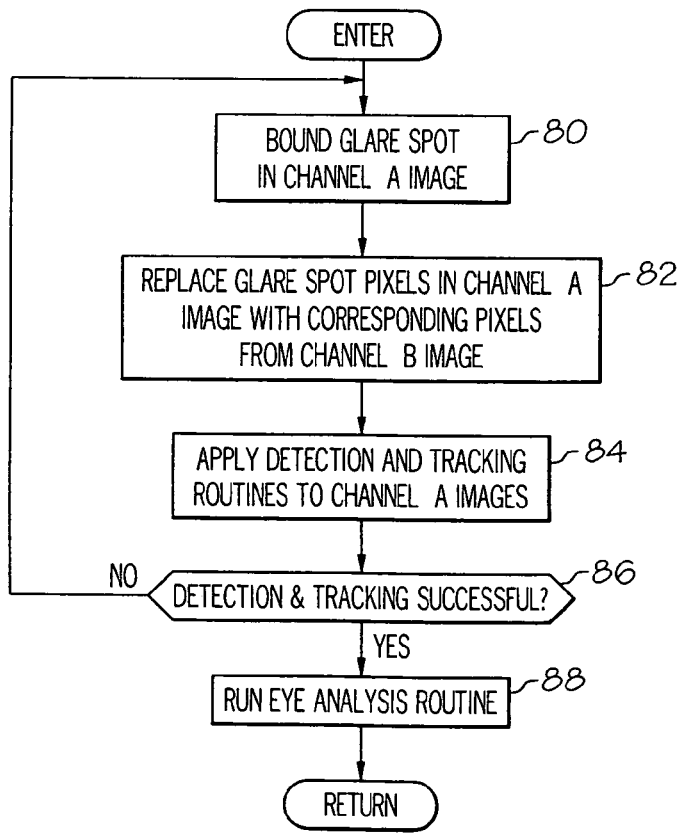
FIG. 5 is a flow diagram representative of an executive routine carried out by the DSP of FIG. 2 for processing the acquired images according to second embodiment of the present invention.
Figure 6:
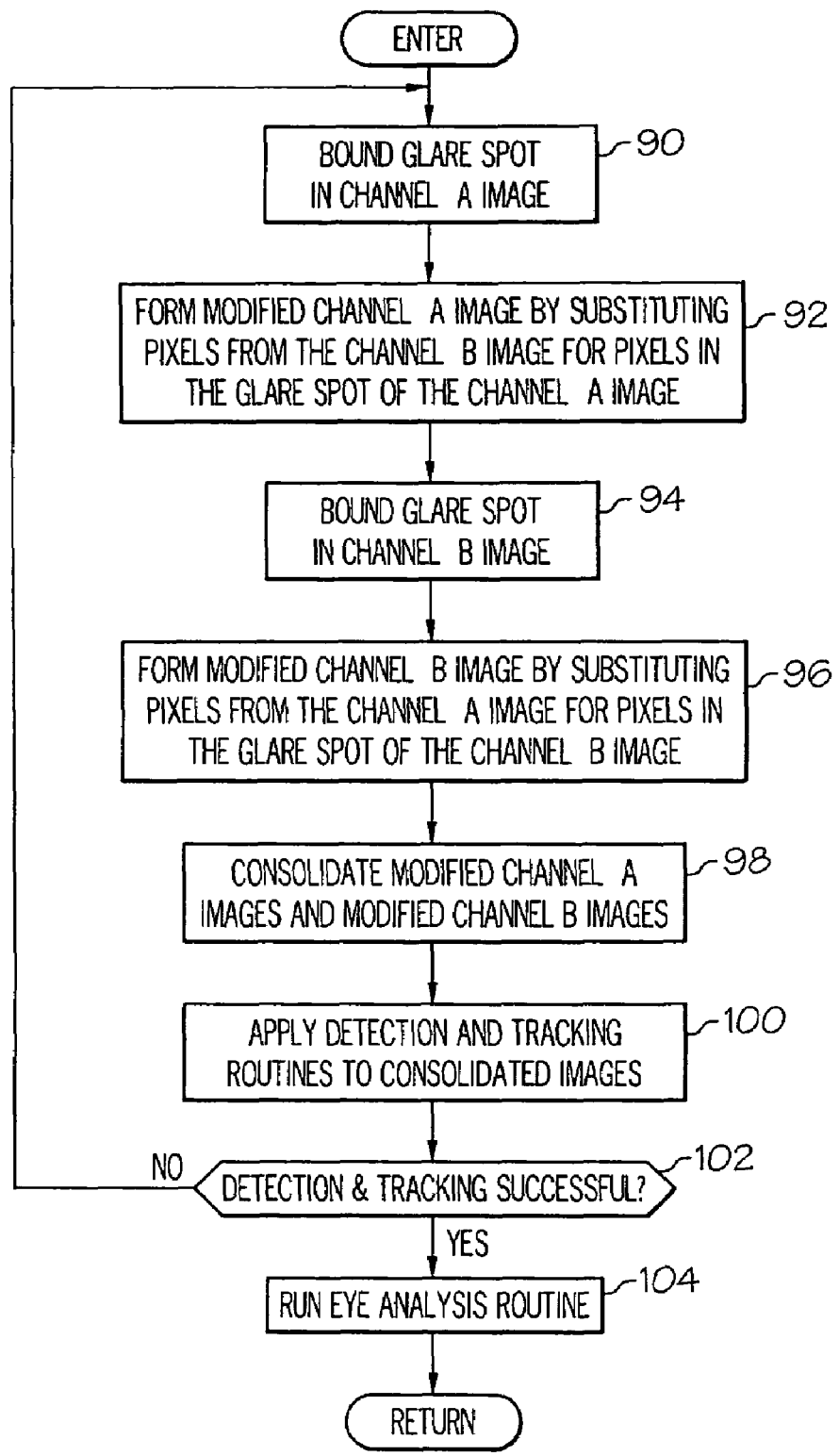
FIG. 6 is a flow diagram representative of an executive routine carried out by the DSP of FIG. 2 for processing the acquired images according to third embodiment of the present invention.

The flow diagrams of FIGS. 4-6 illustrate three possible techniques for processing the Channel_A and Channel_B images developed when DSP 44 executes the flow diagram of FIG. 3.

Referring to FIG. 4, the first processing technique individually applies the detection and tracking routines 50 and 52 to the Channel_A and Channel_B images, as indicated at blocks 70 and 72. If the routines are not successful with the Channel_A images or the Channel_B images, blocks 70-72 are re-executed. If the routines are successful with the images of at least one of the channels, the block 76 is executed to run the eye analysis routine 54.

Referring to FIG. 5, the second processing technique substitutes pixel data from the images of one channel into the images of the other channel to create a series of glare-free images for analysis. The block 80 is first executed to detect and bound a glare spot, if present, in an image assigned to Channel_A (or alternately, Channel_B). The glare spot can be identified, for example, by filtering the eye portion of the image with a morphological bottom-hat filter. The contrast of a local region including the identified spot can be enhanced by histogram equalization. A morphological bottom-hat filter can be applied to the contrast-enhanced region to extract the spot, and the boundary of the glare spot can be defined as the area of overlap between the two filter outputs. Block 82 fetches the corresponding pixel data from a time-adjacent Channel_B image, and substitutes that data into the Channel_A image. The resulting Channel_A image should be substantially glare-free because the glare spot, if present, will be in a different area of the Channel_B image. The block 84 applies the detection and tracking routines to the modified Channel_A images (after defining a search window in the unmodified image based on the previous frame), and the block 86 determines if the routines were successful. If not, the blocks 80-84 are repeated; if so, the block 76 is executed to run the eye analysis routine 54.

Referring to FIG. 6, the third processing technique applies the processing technique of FIG. 5 to the images of both Channel_A and Channnel_B, and then consolidates the modified images for analysis. The blocks 90-92 form a modified Channel_A image by substituting pixels from the Channel_B image for the glare spot pixels of the Channel_A image. Conversely, the blocks 94-96 form a modified Channel_B image by substituting pixels from the Channel_A image for the glare spot pixels of the Channel_B image. The block 98 consolidates the modified Channel_A and Channel_B images to form a succession of glare-free images at the full frame update rate of imaging device 32, thirty frames per second for example. The block 100 applies the detection and tracking routines 50 and 52 to the consolidated stream of images. If block 102 determines that the detection and tracking routines were unsuccessful, the blocks 90-100 are repeated; otherwise, the block 104 is executed to run the eye analysis routine 54.

In summary, the present invention provides a way of reliably detecting and tracking an actively illuminated eye in a series of digital images that are subject to eyeglass glare that occludes the eye. While the invention has been described with respect to the illustrated embodiments, it is recognized that numerous modifications and variations in addition to those mentioned herein will occur to those skilled in the art. For example, system may include more than two sets of active illumination devices, and so on. Accordingly, it is intended that the invention not be limited to the disclosed embodiment, but that it have the full scope permitted by the language of the following claims.

The invention claimed is:

1. A method of monitoring an eye of a human subject based on a succession of digital images captured by an imaging device focused on the subject, comprising the steps of:
   (a) actively illuminating the subject from a first location that is offset from the imaging device and capturing a first image of the subject while so illuminated;
   (b) actively illuminating the subject from a second location that is offset from the imaging device and displaced from said first location, and capturing a second image of the subject while so illuminated;
   (c) processing said first image independent of said second image to detect and track the subject's eye;
   (d) processing the second image independent of said first image to detect and track the subject's eye;
   (e) repeating steps (a)-(d) if neither step (c) nor step (d) was successful; and
   (f) analyzing the detected eye to determine an eye state if at least one of step (c) and step (d) was successful.

2. The method of claim 1, where said first location is above said imaging device and said second location is below said imaging device.

3. The method of claim 1, where said second location is vertically displaced from said first location.

* * * * *